United States Patent
Matheny et al.

(10) Patent No.: US 9,694,104 B2
(45) Date of Patent: *Jul. 4, 2017

(54) VASCULAR CASTED PROSTHESES AND METHODS OF FORMING SAME FOR TREATING BIOLOGICAL TISSUE

(71) Applicant: CorMatrix Cardiovascular, Inc., Roswell, GA (US)

(72) Inventors: Robert G Matheny, Norcross, GA (US); Craig N Ferrante, Bedfordshire (GB)

(73) Assignee: CorMatrix Cardiovascular, Inc., Roswell, GA (US)

(*) Notice: Subject to any disclaimer, the term of this patent is extended or adjusted under 35 U.S.C. 154(b) by 58 days.

This patent is subject to a terminal disclaimer.

(21) Appl. No.: 14/545,096

(22) Filed: Mar. 23, 2015

(65) Prior Publication Data
US 2016/0157983 A1 Jun. 9, 2016

Related U.S. Application Data

(60) Provisional application No. 62/088,987, filed on Dec. 8, 2014.

(51) Int. Cl.
| | |
|---|---|
| *A61L 27/14* | (2006.01) |
| *A61L 27/20* | (2006.01) |
| *A61L 27/36* | (2006.01) |
| *A61L 27/54* | (2006.01) |
| *A61L 27/18* | (2006.01) |
| *A61L 27/16* | (2006.01) |

(Continued)

(52) U.S. Cl.
CPC .............. *A61L 27/20* (2013.01); *A61L 27/16* (2013.01); *A61L 27/18* (2013.01); *A61L 27/3604* (2013.01); *A61L 27/3629* (2013.01); *A61L 27/3633* (2013.01); *A61L 27/3804* (2013.01); *A61L 27/3834* (2013.01); *A61L 27/52* (2013.01); *A61L 27/54* (2013.01); *A61F 2210/0004* (2013.01); *A61F 2210/0057* (2013.01); *A61F 2250/0067* (2013.01); *A61L 2300/41* (2013.01); *A61L 2300/414* (2013.01); *A61L 2300/434* (2013.01); *A61L 2430/00* (2013.01); *A61L 2430/34* (2013.01)

(58) Field of Classification Search
None
See application file for complete search history.

(56) References Cited

U.S. PATENT DOCUMENTS

| | | | | |
|---|---|---|---|---|
| 8,808,352 | B2* | 8/2014 | Eells | ............................ 623/1.13 |
| 2012/0269761 | A1* | 10/2012 | Bettinger | ................ A61L 27/18 424/78.06 |

(Continued)

FOREIGN PATENT DOCUMENTS

WO  WO 2014100718 A1 *  6/2014  ............ D01D 10/02

OTHER PUBLICATIONS

International Consensus. Acellular matrices for the treatment of wounds. An expert working group review. London: Wounds International, 2010.*

*Primary Examiner* — Robert A Wax
*Assistant Examiner* — Melissa Mercier
(74) *Attorney, Agent, or Firm* — Francis Law Group

(57) ABSTRACT

Methods of treating biological tissue with bioremodelable tissue prostheses having a vasculature that is infused with a biomaterial composition.

14 Claims, 7 Drawing Sheets
(5 of 7 Drawing Sheet(s) Filed in Color)

(51) Int. Cl.
*A61L 27/38* (2006.01)
*A61L 27/52* (2006.01)

(56) References Cited

U.S. PATENT DOCUMENTS

| | | | |
|---|---|---|---|
| 2012/0303117 A1* | 11/2012 | Matheny | A61L 27/3633 623/2.15 |
| 2013/0071447 A1* | 3/2013 | Farrell | A61L 27/3633 424/400 |
| 2013/0266549 A1* | 10/2013 | Chenite | A61K 31/722 424/93.7 |
| 2015/0017254 A1* | 1/2015 | Matheny | A61K 38/18 424/574 |

* cited by examiner

VASCULAR CASTED PROSTHESES AND METHODS OF FORMING SAME FOR TREATING BIOLOGICAL TISSUE

CROSS-REFERENCES TO RELATED APPLICATIONS

This application claims the benefit of U.S. Application No. 62/088,987, filed on Dec. 8, 2014.

FIELD OF THE INVENTION

The present invention relates to methods and apparatus for repairing damaged or diseased biological tissue. More particularly, the present invention relates to non-antigenic, resilient, bioremodelable tissue prostheses having a vasculature that is infused with a biomaterial composition and methods of treating damaged biological tissue with the tissue prostheses.

BACKGROUND OF THE INVENTION

As is well known in the art, tissue prostheses are often employed to treat or replace damaged or diseased biological tissue. However, despite the growing sophistication of medical technology, the use of prostheses to treat or replace damaged biological tissue remains a frequent and serious problem in health care. The problem is often associated with the materials employed to construct the prostheses.

As is also well known in the art, the optimal prosthesis material should be chemically inert, non-carcinogenic, capable of resisting mechanical stress, capable of being fabricated in the form required, and sterilizable. Further, the material should be resistant to physical modification by tissue fluids, and not excite an inflammatory reaction, induce a state of allergy or hypersensitivity, or, in some cases, promote visceral adhesions. See, e.g., Jenkins, et al., *Surgery*, vol. 94(2), pp. 392-398 (1983).

Various materials and/or structures have thus been employed to construct prostheses that satisfy the aforementioned optimal characteristics, including tantalum gauze, stainless mesh, Dacron®, Orlon®, Fortisan®, nylon, knitted polypropylene (e.g., Marlex®), microporous expanded-polytetrafluoroethylene (e.g., Gore-Tex®), Dacron reinforced silicone rubber (e.g., Silastic®), polyglactin 910 (e.g., Vicryl®), polyester (e.g., Mersilene®), polyglycolic acid (e.g., Dexon®), processed sheep dermal collagen, crosslinked bovine pericardium (e.g., Peri-Guard®), and preserved human dura (e.g., Lyodura®).

As discussed in detail below, although some of the noted prosthesis materials satisfy some of the aforementioned optimal characteristics, there are several disadvantages and drawbacks associated with the materials.

The major advantages of metallic reinforced prostheses, e.g., stainless steel and Nitinol® meshes, are that they are inert, resistant to infection and can stimulate fibroplasia. Several major disadvantages are fragmentation, which can, and in many instances will, occur after the first year of administration, and the lack of malleability.

Further, many conventional prostheses; particularly, stents are often constructed from various polymeric materials, such as poly(ethylene terephthalate) (PET). Such prostheses often cause irritation and undesirable biologic responses from the surrounding tissues in a vessel.

Although conventional prostheses are designed to be implanted for an extended period of time, it is sometimes necessary to remove the device prematurely, for example, because of poor patency or harsh biological responses. In such instances, the device generally must be removed through a secondary surgical procedure, which can, and in many instances will, result in undesirable pain and discomfort to the patient and possibly additional trauma to the vessel tissue. In addition to the pain and discomfort, the patient must be subjected to an additional time consuming and complicated surgical procedure with the attendant risks of surgery.

More recently, bioabsorbable and/or biodegradable prostheses have been developed in an effort to eliminate the harsh biological responses associated with conventional polymeric and metal vascular prostheses. There are, however, several known disadvantages associated with bioabsorbable and biodegradable prostheses.

One major disadvantage is that the bioabsorbable and biodegradable materials and, hence, prostheses often break down at a faster rate than is desirable for the application. A further disadvantage is that the bioabsorbable and biodegradable materials can, and in many instances will, break down into large, rigid fragments that can cause obstructions in the interior of a vessel.

A further disadvantage associated with conventional prostheses is that existing means for securing the prosthesis into or onto biological tissue within a body vessel have had limited success. Often the securing means comprises engaging the prosthesis to the surrounding tissue by physical or mechanical means, such as disclosed in U.S. Pat. No. 7,918,882. Another securing means comprises modifying the prosthesis surface or material to induce the production of fibrous (scar) tissue to anchor the prosthesis upon implantation within the vessel.

Various polymer based apparatus have also been developed in an attempt to construct reinforced prostheses. Illustrative are the ECM and polymer based apparatus, i.e. grafts and endografts, disclosed in U.S. Pat. Nos. 6,015,432 and 8,142,506.

U.S. Pat. No. 6,015,432 discloses a fiber-reinforced hydrogel prosthesis that is intended to replace cartilaginous materials, wherein the fibers comprise a polymeric material, such as polyurethane fibers.

U.S. Pat. No. 8,142,506 discloses an endovascular tube or bifurcated prosthesis comprising a polymeric material reinforced by a threaded superelastic metal wire, such as a Nitinol®.

A major drawback of the noted polymer based apparatus, as well as most known apparatus, is that the apparatus often comprise or include a permanent structure that remains in the body, i.e. non-biodegradable. As is well known in the art, such structures (or devices) can, and in most instances will, cause irritation and undesirable biologic responses in the surrounding tissue.

Such structures (and devices) are also prone to failure, resulting in severe adverse consequences, e.g., ruptured vessels.

There is thus a need to provide improved prostheses that substantially reduce or eliminate (i) intimal hyperplasia after intervention in a vessel, (ii) the harsh biological responses associated with conventional, and (iii) employ effective vessel securing means.

There is also a need to provide prostheses that can replace or improve biological functions or promote the growth of new tissue in a subject.

There is also a need to provide prostheses that substantially reduce or eliminate the formation of inflammation and infection.

There is also the need to provide prostheses having mechanical compatibility or enhanced mechanical properties. As is well known in the art, a mismatch between the stiffness, hardness, and porosity of a prosthesis in comparison to the surrounding tissue environment can cause irritation and other complications after implantation.

It is therefore an object of the present invention to provide prostheses that substantially reduce or eliminate (i) intimal hyperplasia after intervention in a vessel, (ii) the harsh biological responses associated with conventional polymeric and metal prostheses, (iii) employ effective vessel securing means, and (iv) the formation of biofilm, inflammation and infection.

It is another object of the present invention to provide prostheses that can effectively replace or improve biological functions or promote the growth of new tissue in a subject.

It is another object of the present invention to provide prostheses that include effective reinforcing means for temporarily positioning the prostheses proximate target tissue and retaining strength.

It is another object of the present invention to provide prostheses that can administer one or more pharmacological or therapeutic agents to a subject.

It is another object of the present invention to provide methods of treating damaged biological tissue with tissue prostheses that are configured to improve biological functions and/or promote the growth of new tissue in a subject, referred to herein as "modulated healing."

SUMMARY OF THE INVENTION

The present invention is directed to casted constructs for treating, reconstructing or replacing damaged or diseased biological tissue.

As discussed in detail herein, in a preferred embodiment, the casted constructs comprise an ECM member having a biomaterial composition disposed within the vasculature of the ECM member.

In some embodiments of the invention, the casted constructs comprise a seamless ECM material derived from a mammalian tissue source. According to the invention, the seamless ECM material can be derived from various mammalian tissue sources, including, without limitation, small intestine, large intestine and umbilical cord.

In some embodiments of the invention, the casted constructs comprise a seamed ECM material derived from a mammalian tissue source. According to the invention, the ECM material can similarly be derived from various mammalian tissue sources. In some embodiments of the invention, the mammalian tissue sources include, without limitation, the small intestine, large intestine, stomach, lung, liver, kidney, pancreas, placenta, heart, bladder, prostate, tissue surrounding growing enamel, tissue surrounding growing bone, and any fetal tissue from any mammalian organ.

In a preferred embodiment, the mammalian ECM material referenced above comprises sterilized acellular ECM material.

Preferably, the mammalian tissue sources referenced above comprise an adolescent mammalian tissue source.

In some embodiments, the biomaterial composition comprises an ECM-mimicking biomaterial composition, such as poly(glycerol sebacate) (PGS).

In some embodiments of the invention, the biomaterial composition comprises a polymeric composition further comprising a biocompatible polymeric material, such as poly(ε-caprolactone) (PCL).

In some embodiments of the invention, the biomaterial composition comprises an ECM composition comprising at least one ECM material.

In some embodiments of the invention, the ECM material and/or biomaterial composition and, hence, casted constructs formed therewith further comprise at least one additional biologically active agent or composition, i.e. an agent that induces or modulates a physiological or biological process, or cellular activity, e.g., induces proliferation, and/or growth and/or regeneration of tissue.

In some embodiments, the biologically active agent comprises a cell, such as, without limitation, a human embryonic stem cell, fetal cardiomyocyte, myofibroblast, and mesenchymal stem cell.

In some embodiments, the biologically active agent comprises a growth factor, such as, without limitation, a transforming growth factor-alpha (TGF-α), transforming growth factor-beta (TGF-β, fibroblast growth factor-2 (FGF-2), basic fibroblast growth factor (bFGF), and vascular epithelial growth factor (VEGF).

In some embodiments, the ECM material and/or biomaterial composition, and, hence, casted constructs formed therewith further comprise at least one pharmacological agent or composition (or drug), i.e. an agent or composition that is capable of producing a desired biological effect in vivo, e.g., stimulation or suppression of apoptosis, stimulation or suppression of an immune response, etc.

Suitable pharmacological agents and compositions include, without limitation, antibiotics, anti-viral agents, analgesics, anti-inflammatories, anti-neoplastics, anti-spasmodics, and anticoagulants and/or anti-thrombic agents.

In some embodiments of the invention, the pharmacological agent comprises a statin, i.e. a HMG-CoA reductase inhibitor, such as cerivastatin.

In some embodiments of the invention, the casted constructs further comprise an outer reinforcing structure.

In some embodiments of the invention, the reinforcing structure comprises a thin member, such as a strand, that is wound about the outer surface of the casted construct.

In some embodiments of the invention, the reinforcing structure comprises a mesh or woven structure.

In some embodiments of the invention, the reinforcing structure comprises an ECM-mimicking biomaterial, such as PGS.

In some embodiments, the casted constructs are incubated in a macerating agent to degrade the ECM member.

In another embodiment of the invention, there is provided a method of forming the aforementioned casted constructs of the invention.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Further features and advantages will become apparent from the following and more particular description of the preferred embodiments of the invention, as illustrated in the accompanying drawings, and in which like referenced characters generally refer to the same parts or elements throughout the views, and in which.

DETAILED DESCRIPTION OF THE PREFERRED EMBODIMENT

Figure 1:
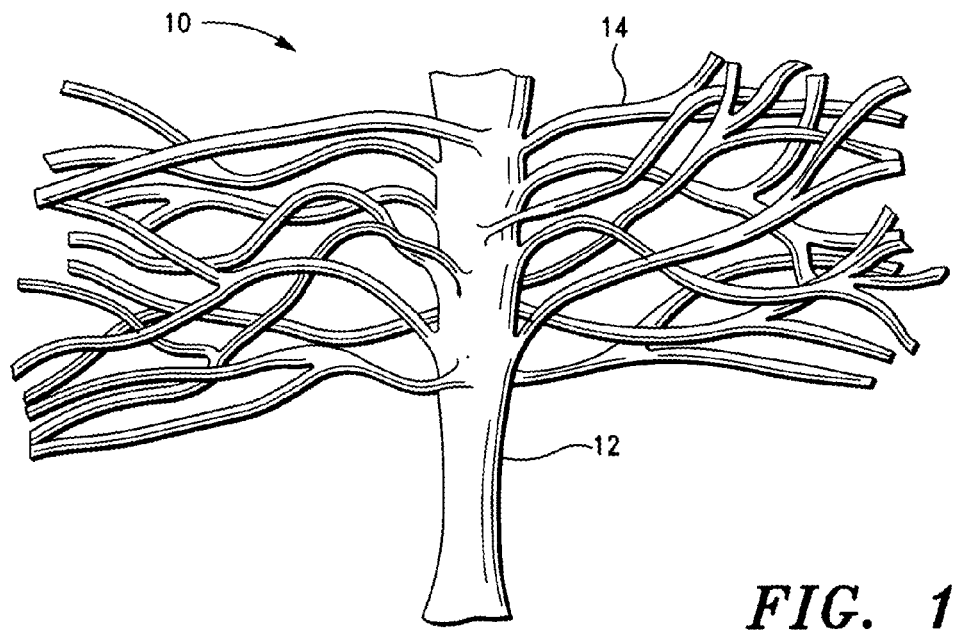
FIG. 1 is an illustration of a mammalian small intestine vasculature.

Before describing the present invention in detail, it is to be understood that this invention is not limited to particularly exemplified apparatus, systems, materials, compositions, structures or methods as such may, of course, vary. Thus, although a number of apparatus, systems, materials, compositions, structures and methods similar or equivalent to those described herein can be used in the practice of the present invention, the preferred apparatus, systems, materials, compositions, structures and methods are described herein.

It is also to be understood that the terminology used herein is for the purpose of describing particular embodiments of the invention only and is not intended to be limiting.

Unless defined otherwise, all technical and scientific terms used herein have the same meaning as commonly understood by one having ordinary skill in the art to which the invention pertains.

Further, all publications, patents and patent applications cited herein, whether supra or infra, are hereby incorporated by reference in their entirety.

As used in this specification and the appended claims, the singular forms "a, "an" and "the" include plural referents unless the content clearly dictates otherwise. Thus, for example, reference to "an active" includes two or more such actives and the like.

Further, ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

It is also understood that there are a number of values disclosed herein, and that each value is also herein disclosed as "approximately" that particular value in addition to the value itself. For example, if the value "10" is disclosed, then "approximately 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed then "less than or equal to 10", as well as "greater than or equal to 10" is also disclosed.

Definitions

The terms "prosthesis" and "casted construct" are used interchangeably herein, and mean and include a structure or system that is configured for placement on biological tissue on or in an organ, such as a lumen or vessel. As discussed in detail herein, upon placement of a biological prostheses or casted construct of the invention to biological tissue; particularly, damaged or diseased tissue, the casted construct induces "modulated healing", as defined herein.

The term "biocompatible", as used herein, means a device or material that is substantially non-toxic in an in vivo environment, and is not substantially rejected by a recipient's physiological system, i.e. non-antigenic.

The terms "cast" and "casted" are used interchangeably herein, and mean and include a structure comprising a configuration or shape provided by a cast or mold template, e.g., the vasculature of biological tissue.

The term "buffer", as used herein, means a composition, preferably a solution that resists changes in pH when acid or alkali is added to it. Buffers typically comprise a weak acid or alkali together with one of its salts.

The terms "vascular" and "vasculature" are used interchangeably herein, and mean and include a structure of, relating to, affecting, or comprising a vessel or vessels; particularly, a vessel or vessels that transport blood.

The term "kinetics" as used herein, means and refers to the rates of chemical and/or biochemical reactions, including the rates of multiple simultaneous or overlapping reactions, which may be directly or indirectly related, e.g. the activation of growth factors and/or cytokines.

The term "macerated" as used herein, means and refers to the gradual degradation of a polymeric or biological composition through chemical, enzymatic and/or mechanical means.

The terms "extracellular matrix" and "ECM" are used interchangeably herein, and mean and include a collagen-rich substance that is found in between cells in mammalian tissue, and any material processed therefrom, e.g. decellularized ECM. According to the invention, the ECM material can be derived from various mammalian tissue sources including, without limitation, the small intestine, large intestine, stomach, lung, liver, kidney, pancreas, placenta, heart, bladder, prostate, tissue surrounding growing enamel, tissue surrounding growing bone, and any fetal tissue from any mammalian organ.

The ECM material can thus comprise, without limitation, small intestine submucosa (SIS), urinary bladder submucosa (UBS), stomach submucosa (SS), central nervous system tissue, dermal extracellular matrix, subcutaneous extracellular matrix, gastrointestinal extracellular matrix, i.e. large and small intestines, tissue surrounding growing bone, placental extracellular matrix, omentum extracellular matrix, epithelium of mesodermal origin, i.e. mesothelial tissue, cardiac extracellular matrix, e.g., pericardium and/or myocardium, kidney extracellular matrix, pancreas extracellular matrix, lung extracellular matrix, and combinations thereof. The ECM can also comprise collagen from mammalian sources.

The terms "urinary bladder submucosa (UBS)", "small intestine submucosa (SIS)" and "stomach submucosa (SS)" also mean and include any UBS and/or SIS and/or SS material that includes the tunica mucosa (which includes the transitional epithelial layer and the tunica propria), submucosal layer, one or more layers of muscularis, and adventitia (a loose connective tissue layer) associated therewith.

The ECM can also be derived from basement membrane of mammalian tissue/organs, including, without limitation, bladder, "urinary basement membrane (UBM)", liver, i.e. "liver basement membrane (LBM)", and amnion, chorion, allograft pericardium, allograft acellular dermis, amniotic membrane, Wharton's jelly, and combinations thereof.

Additional sources of mammalian basement membrane include, without limitation, spleen, lymph nodes, salivary glands, prostate, pancreas and other secreting glands.

The ECM can also be derived from other sources, including, without limitation, collagen from plant sources and synthesized extracellular matrices, i.e. cell cultures.

The term "angiogenesis", as used herein, means a physiologic process involving the growth of new blood vessels from pre-existing blood vessels.

The term "neovascularization", as used herein, means and includes the formation of functional vascular networks that can be perfused by blood or blood components. Neovascularization includes angiogenesis, budding angiogenesis, intussuceptive angiogenesis, sprouting angiogenesis, therapeutic angiogenesis and vasculogenesis.

The terms "ECM-mimicking biomaterial", and "ECM-mimicking material" are used interchangeably herein, and mean and include a biocompatible and biodegradable biomaterial that induces neovascularization and bioremodeling of tissue in vivo, i.e. when disposed proximate damaged biological tissue. The term "ECM-mimicking" thus includes, without limitation, ECM-mimicking polymeric biomaterial compositions; specifically, poly(glycerol sebacate) (PGS).

The terms "biologically active agent" and "biologically active composition" are used interchangeably herein, and mean and include agent that induces or modulates a physiological or biological process, or cellular activity, e.g., induces proliferation, and/or growth and/or regeneration of tissue.

The terms "biologically active agent" and "biologically active composition" thus mean and include, without limitation, the following growth factors: platelet derived growth factor (PDGF), epidermal growth factor (EGF), transforming growth factor alpha (TGF-α), transforming growth factor beta (TGF-β), fibroblast growth factor-2 (FGF-2), basic fibroblast growth factor (bFGF), vascular epithelial growth factor (VEGF), hepatocyte growth factor (HGF), insulin-like growth factor (IGF), nerve growth factor (NGF), platelet derived growth factor (PDGF), tumor necrosis factor alpha (TNF-α), and placental growth factor (PLGF).

The terms "biologically active agent" and "biologically active composition" also mean and include, without limitation, embryonic stem cells, mesenchymal stem cells, hematopoietic stem cells, bone marrow stem cells, bone marrow-derived progenitor cells, myosatellite progenitor cells, totipotent stem cells, pluripotent stem cells, multipotent stem cells, oligopotent stem cells and unipotent stem cells. The group also comprises cardiomyocytes, myoblasts, monocytes, parenchymal cells, epithelial cells, endothelial cells, mesothelial cells, fibroblasts, osteoblasts, chondrocytes, exogenous cells, endogenous cells, macrophages, capillary endothelial cells, autologous cells, xenogenic cells, allogenic cells, and cells derived from any of the three germ layers including the endoderm, mesoderm and ectoderm.

The terms "biologically active agent" and "biologically active composition" also mean and include, without limitation, the following biologically active agents (referred to interchangeably herein as a "protein", "peptide" and "polypeptide"): collagen (types I-V), proteoglycans, glycosaminoglycans (GAGs), glycoproteins, cytokines, cell-surface associated proteins, cell adhesion molecules (CAM), endothelial ligands, matrikines, cadherins, immuoglobins, fibril collagens, non-fibrillar collagens, basement membrane collagens, multiplexins, small-leucine rich proteoglycans, decorins, biglycans, fibromodulins, keratocans, lumicans, epiphycans, heparin sulfate proteoglycans, perlecans, agrins, testicans, syndecans, glypicans, serglycins, selectins, lecticans, aggrecans, versicans, neurocans, brevicans, cytoplasmic domain-44 (CD-44), macrophage stimulating factors, amyloid precursor proteins, heparins, chondroitin sulfate B (dermatan sulfate), chondroitin sulfate A, heparin sulfates, hyaluronic acids, fibronectins, tenascins, elastins, fibrillins, laminins, nidogen/enactins, fibulin I, fibulin II, integrins, transmembrane molecules, thrombospondins, ostepontins, and angiotensin converting enzymes (ACE).

The terms "pharmacological agent", "active agent", "drug" and "active agent formulation" are used interchangeably herein, and mean and include an agent, drug, compound, composition of matter or mixture thereof, including its formulation, which provides some therapeutic, often beneficial, effect. This includes any physiologically or pharmacologically active substance that produces a localized or systemic effect or effects in animals, including warm blooded mammals, humans and primates; avians; domestic household or farm animals, such as cats, dogs, sheep, goats, cattle, horses and pigs; laboratory animals, such as mice, rats and guinea pigs; fish; reptiles; zoo and wild animals; and the like.

The terms "pharmacological agent", "active agent", "drug" and "active agent formulation" thus mean and include, without limitation, antibiotics, anti-arrhythmic agents, anti-viral agents, analgesics, steroidal anti-inflammatories, non-steroidal anti-inflammatories, anti-neoplastics, anti-spasmodics, modulators of cell-extracellular matrix interactions, proteins, hormones, growth factors, matrix metalloproteinases (MMPs), enzymes and enzyme inhibitors, anticoagulants and/or anti-thrombic agents, DNA, RNA, modified DNA and RNA, NSAIDs, inhibitors of DNA, RNA or protein synthesis, polypeptides, oligonucleotides, polynucleotides, nucleoproteins, compounds modulating cell migration, compounds modulating proliferation and growth of tissue, and vasodilating agents.

The terms "pharmacological agent", "active agent", "drug" and "active agent formulation" thus include, without limitation, atropine, tropicamide, dexamethasone, dexamethasone phosphate, betamethasone, betamethasone phosphate, prednisolone, triamcinolone, triamcinolone acetonide, fluocinolone acetonide, anecortave acetate, budesonide, cyclosporine, FK-506, rapamycin, ruboxistaurin, midostaurin, flurbiprofen, suprofen, ketoprofen, diclofenac, ketorolac, nepafenac, lidocaine, neomycin, polymyxin b, bacitracin, gramicidin, gentamicin, oyxtetracycline, ciprofloxacin, ofloxacin, tobramycin, amikacin, vancomycin, cefazolin, ticarcillin, chloramphenicol, miconazole, itraconazole, trifluridine, vidarabine, ganciclovir, acyclovir, cidofovir, ara-amp, foscarnet, idoxuridine, adefovir dipivoxil, methotrexate, carboplatin, phenylephrine, epinephrine, dipivefrin, timolol, 6-hydroxydopamine, betaxolol, pilocarpine, carbachol, physostigmine, demecarium, dorzolamide, brinzolamide, latanoprost, sodium hyaluronate, insulin, verteporfin, pegaptanib, ranibizumab, and other antibodies, antineoplastics, anti-VEGFs, ciliary neurotrophic factor, brain-derived neurotrophic factor, bFGF, Caspase-1 inhibitors, Caspase-3 inhibitors, α-Adrenoceptors agonists, NMDA antagonists, Glial cell line-derived neurotrophic factors (GDNF), pigment epithelium-derived factor (PEDF), and NT-3, NT-4, NGF, IGF-2.

The terms "pharmacological agent", "active agent", "drug" and "active agent formulation" further mean and include the following Class I-Class V anti-arrhythmic agents: (Class Ia) quinidine, procainamide and disopyramide; (Class Ib) lidocaine, phenytoin and mexiletine; (Class Ic) flecainide, propafenone and moricizine; (Class II) propranolol, esmolol, timolol, metoprolol and atenolol; (Class III) amiodarone, sotalol, ibutilide and dofetilide; (Class IV) verapamil and diltiazem and (Class V) adenosine and digoxin.

The terms "pharmacological agent", "active agent", "drug" and "active agent formulation" further mean and include, without limitation, the following antibiotics: aminoglycosides, cephalosporins, chloramphenicol, clindamycin, erythromycins, fluoroquinolones, macrolides, azolides, metronidazole, penicillins, tetracyclines, trimethoprim-sulfamethoxazole and vancomycin.

The terms "pharmacological agent", "active agent", "drug" and "active agent formulation" further include, without limitation, the following steroids: andranes (e.g., testosterone), cholestanes, cholic acids, corticosteroids (e.g., dexamethasone), estraenes (e.g., estradiol) and pregnanes (e.g., progesterone).

The terms "pharmacological agent", "active agent", "drug" and "active agent formulation" can further include one or more classes of narcotic analgesics, including, without limitation, morphine, codeine, heroin, hydromorphone, levorphanol, meperidine, methadone, oxycodone, propoxyphene, fentanyl, methadone, naloxone, buprenorphine, butorphanol, nalbuphine and pentazocine.

The terms "pharmacological agent", "active agent", "drug" and "active agent formulation" can further include one or more classes of topical or local anesthetics, including, without limitation, esters, such as benzocaine, chloroprocaine, cocaine, cyclomethycaine, dimethocaine/larocaine, piperocaine, propoxycaine, procaine/novacaine, proparacaine, and tetracaine/amethocaine. Local anesthetics can also include, without limitation, amides, such as articaine, bupivacaine, cinchocaine/dibucaine, etidocaine, levobupivacaine, lidocaine/lignocaine, mepivacaine, prilocaine, ropivacaine, and trimecaine. Local anesthetics can further include combinations of the above from either amides or esters.

The terms "anti-inflammatory" and "anti-inflammatory agent" are also used interchangeably herein, and mean and include a "pharmacological agent" and/or "active agent formulation", which, when a therapeutically effective amount is administered to a subject, prevents or treats bodily tissue inflammation i.e. the protective tissue response to injury or destruction of tissues, which serves to destroy, dilute, or wall off both the injurious agent and the injured tissues.

Anti-inflammatory agents thus include, without limitation, alclofenac, alclometasone dipropionate, algestone acetonide, alpha amylase, amcinafal, amcinafide, amfenac sodium, amiprilose hydrochloride, anakinra, anirolac, anitrazafen, apazone, balsalazide disodium, bendazac, benoxaprofen, benzydamine hydrochloride, bromelains, broperamole, budesonide, carprofen, cicloprofen, cintazone, cliprofen, clobetasol propionate, clobetasone butyrate, clopirac, cloticasone propionate, cormethasone acetate, cortodoxone, decanoate, deflazacort, delatestryl, depo-testosterone, desonide, desoximetasone, dexamethasone dipropionate, diclofenac potassium, diclofenac sodium, diflorasone diacetate, diflumidone sodium, diflunisal, difluprednate, diftalone, dimethyl sulfoxide, drocinonide, endrysone, enlimomab, enolicam sodium, epirizole, etodolac, etofenamate, felbinac, fenamole, fenbufen, fenclofenac, fenclorac, fendosal, fenpipalone, fentiazac, flazalone, fluazacort, flufenamic acid, flumizole, flunisolide acetate, flunixin, flunixin meglumine, fluocortin butyl, fluorometholone acetate, fluquazone, flurbiprofen, fluretofen, fluticasone propionate, furaprofen, furobufen, halcinonide, halobetasol propionate, halopredone acetate, ibufenac, ibuprofen, ibuprofen aluminum, ibuprofen piconol, ilonidap, indomethacin, indomethacin sodium, indoprofen, indoxole, intrazole, isoflupredone acetate, isoxepac, isoxicam, ketoprofen, lofemizole hydrochloride, lomoxicam, loteprednol etabonate, meclofenamate sodium, meclofenamic acid, meclorisone dibutyrate, mefenamic acid, mesalamine, meseclazone, mesterolone, methandrostenolone, methenolone, methenolone acetate, methylprednisolone suleptanate, momiflumate, nabumetone, nandrolone, naproxen, naproxen sodium, naproxol, nimazone, olsalazine sodium, orgotein, orpanoxin, oxandrolane, oxaprozin, oxyphenbutazone, oxymetholone, paranyline hydrochloride, pentosan polysulfate sodium, phenbutazone sodium glycerate, pirfenidone, piroxicam, piroxicam cinnamate, piroxicam olamine, pirprofen, prednazate, prifelone, prodolic acid, proquazone, proxazole, proxazole citrate, rimexolone, romazarit, salcolex, salnacedin, salsalate, sanguinarium chloride, seclazone, sermetacin, stanozolol, sudoxicam, sulindac, suprofen, talmetacin, talniflumate, talosalate, tebufelone, tenidap, tenidap sodium, tenoxicam, tesicam, tesimide, testosterone, testosterone blends, tetrydamine, tiopinac, tixocortol pivalate, tolmetin, tolmetin sodium, triclonide, triflumidate, zidometacin, and zomepirac sodium.

The term "pharmacological composition", as used herein, means and includes a composition comprising a "pharmacological agent" and/or a "biologically active agent" and/or any additional agent or component identified herein.

The term "ECM composition", as used herein, means and includes a composition comprising at least one ECM.

The term "therapeutically effective", as used herein, means that the amount of the "pharmacological composition" and/or "pharmacological agent" and/or "biologically active agent" administered is of sufficient quantity to ameliorate one or more causes, symptoms, or sequelae of a disease or disorder. Such amelioration only requires a reduction or alteration, not necessarily elimination, of the cause, symptom, or sequelae of a disease or disorder.

The terms "prevent" and "preventing" are used interchangeably herein, and mean and include reducing the frequency or severity of a disease or condition. The term does not require an absolute preclusion of the disease or condition. Rather, this term includes decreasing the chance for disease occurrence.

The terms "treat" and "treatment" are used interchangeably herein, and mean and include medical management of a patient with the intent to cure, ameliorate, stabilize, or prevent a disease, pathological condition, or disorder. The terms include "active treatment", i.e. treatment directed specifically toward the improvement of a disease, pathological condition, or disorder, and "causal treatment", i.e. treatment directed toward removal of the cause of the associated disease, pathological condition, or disorder.

The terms "treat" and "treatment" further include "palliative treatment", i.e. treatment designed for the relief of symptoms rather than the curing of the disease, pathological condition, or disorder, "preventative treatment", i.e. treatment directed to minimizing or partially or completely inhibiting the development of the associated disease, pathological condition, or disorder, and "supportive treatment", i.e. treatment employed to supplement another specific therapy directed toward the improvement of the associated disease, pathological condition, or disorder.

The terms "optional" and "optionally" mean that the subsequently described event, circumstance, or material may or may not occur or be present, and that the description includes instances where the event, circumstance, or material occurs or is present and instances where it does not occur or is not present.

The terms "patient" and "subject" are used interchangeably herein, and mean and include warm blooded mammals, humans and primates; avians; domestic household or farm animals, such as cats, dogs, sheep, goats, cattle, horses and pigs; laboratory animals, such as mice, rats and guinea pigs; fish; reptiles; zoo and wild animals; and the like.

The term "comprise" and variations of the term, such as "comprising" and "comprises," means "including, but not limited to" and is not intended to exclude, for example, other additives, components, integers or steps.

The following disclosure is provided to further explain in an enabling fashion the best modes of performing one or more embodiments of the present invention. The disclosure is further offered to enhance an understanding and appreciation for the inventive principles and advantages thereof, rather than to limit in any manner the invention. The invention is defined solely by the appended claims including any amendments made during the pendency of this application and all equivalents of those claims as issued.

In overview, the present disclosure is directed to nonantigenic, resilient, biodegradable biological prostheses, i.e. bioremodelable vascular casted constructs, which are reinforced via perfusion of a biomaterial composition in the vasculature of the construct.

In some embodiments of the invention, the ECM member comprises a seamless tubular ECM member comprising ECM material derived from a mammalian tissue source.

According to the invention, the seamless tubular members of the invention can comprise any mammalian tubular structure, including, without limitation, a segment of a large or small intestine, umbilical artery or vein, ureter, mesenteric vessel and jugular vein.

According to the invention, the seamless member can thus comprise, without limitation, SIS, SS, gastrointestinal extracellular matrix and umbilical cord extracellular matrix.

In some embodiments, the seamless member can also comprise mesothelial tissue.

In some embodiments, the ECM member comprises a planar ECM member comprising ECM material derived from a mammalian tissue source.

In some embodiments, the planar ECM member comprises a seamed tubular ECM member comprising ECM material derived from a mammalian tissue source.

According to the invention, the planar and tubular member mammalian tissue sources include, without limitation, the small intestine, large intestine, stomach, lung, liver, kidney, pancreas, placenta, heart, bladder, prostate, tissue surrounding growing enamel, tissue surrounding growing bone, and any fetal tissue from any mammalian organ.

The planar and tubular member (seamless and seamed) ECM material can thus comprise ECM selected from the group comprising, without limitation, SIS, UBS, SS, central nervous system tissue, dermal extracellular matrix, subcutaneous extracellular matrix, gastrointestinal extracellular matrix, tissue surrounding growing bone, placental extracellular matrix, omentum extracellular matrix, mesothelial tissue, cardiac extracellular matrix, kidney extracellular matrix, pancreas extracellular matrix, lung extracellular matrix, and combinations thereof.

In some embodiments, the planar and tubular member ECM comprises mesothelial tissue.

In a preferred embodiment, the casted construct, i.e. planar or tubular member, mammalian tissue source comprises an adolescent mammalian tissue source, i.e. an adolescent mammal, such as a piglet, which is preferably less than three (3) years of age.

The casted construct ECM material can also be derived from the same or different mammalian tissue sources, as disclosed in Co-Pending application Ser. Nos. 13/033,053 and 13/033,102; which are incorporated by reference herein.

According to the invention, the casted construct ECM material can be used in whole or in part, so that, for example, an ECM material can contain just the basement membrane (or transitional epithelial layer) with the subadjacent tunica propria, the tunica submucosa, tunica muscularis, and tunica serosa. The ECM material component of the composition can contain any or all of these layers, and thus could conceivably contain only the basement membrane portion, excluding the submucosa. However, generally, and especially since the submucosa is thought to contain and support the active growth factors and other proteins necessary for in vivo tissue regeneration, the ECM or matrix composition from any given source will contain the active extracellular matrix portions that support cell development and differentiation and tissue regeneration.

In some embodiments, the casted construct ECM material comprises the submucosal layer.

In some embodiments, the casted construct ECM material comprises the epithelial basement membrane.

In some embodiments, the casted construct ECM material comprises the submucosal and the mucosal layers further comprising the muscularis mucosa therebetween.

In some embodiments, the casted construct ECM material comprises the submucosal, mucosal and muscularis layers.

In some embodiments the casted construct ECM material comprises the submucosal, mucosal, muscularis and serosa layers.

According to the invention, any of the aforementioned layers of the casted construct ECM material can be delaminated to accommodate various structures and applications.

In a preferred embodiment, the casted construct ECM Material comprises sterilized acellular ECM material.

According to the invention, the casted construct ECM material can be sterilized via applicant's proprietary Novasterilis® processes disclosed in U.S. Pat. No. 7,108,832 and U.S. patent application Ser. Nos. 13/267,337 and 13/480,205; which are incorporated by reference herein in their entirety.

As set forth in U.S. application Ser. No. 13/480,205, additional biologically active and pharmacological agents can be disposed on and/or incorporated (or diffused) into the casted ECM constructs of the invention.

According to the invention, the casted construct ECM material can also be sterilized via the perfusion of a sterilant delivered into the vasculature.

In some embodiments, the sterilant comprises a sterilant composition comprising at least one sterilant.

According to the invention, suitable sterilants include, without limitation, acetic acid and chemical derivatives thereof, peracetic acid, trifluoroacetic acid, hydrogen peroxide, glutaraldehyde and combinations thereof.

In some embodiments, the sterilant composition comprises a Sporeclenz® sterilant, i.e. a mixture comprising acetic acid, hydrogen peroxide, and peracetic acid.

Preferably, the Sporeclenz® sterilant composition is delivered into the vasculature in a sterilization-enhancing effective amount in the range of approximately 0.001-2.0 vol. %.

In some embodiments, the sterilant composition comprises a peracetic acid composition further comprising an organic alcohol including, without limitation, ethyl alcohol, isopropyl alcohol and methanol.

Preferably, the alcohol concentration of the peracetic acid composition is in the range of approximately 1-99.9 vol. %, more preferably, in the range of approximately 5-20 vol. %.

In some embodiments, the sterilant composition comprises at least one detergent.

According to the invention, suitable detergents include, without limitation, non-ionic detergents selected from the group comprising zwitter ionic detergents, deoxycholic acid, triton X-100, Tween 20, brij 58, brij 96, brij 98, lubrol WX, CHAPS (3-[(3-cholamidopropyl)dimethylammonio]-1-propanesulfonate) and combinations thereof.

In a preferred embodiment, the casted construct ECM material vasculature is perfused with a detergent composition prior to perfusion with at least one additional sterilant composition, such as peracetic acid.

Applicant has found that the perfusion of a detergent throughout the vasculature prior to perfusion provides at least 98% removal of raw DNA content compared to 94% removal of raw DNA content from treatment comprising the perfusion of a sterilant/alcohol composition prior to treatment with a detergent composition.

In some embodiments, the casted construct ECM material vasculature is perfused with at least one additional sterilant composition, such as, by way of example, peracetic acid, prior to perfusion with the detergent composition.

In some embodiments, the casted construct ECM material is incubated for 24 to 48 hours in 0.5-1% Triton X-100 and 0.5-1% Deoxycholic acid with 5 mM EDTA in Dulbecco's Phosphate Buffered Saline (DPBS). In this aspect, it is contemplated that flat or sheet-like casted construct ECM materials, such as stomach submucosa (SS), small intestine submucosa (SIS), and bladder submucosa (UBS), can be incubated in a stretched configuration. It is further contemplated that the casted construct ECM member (or material) vasculature can be perfused with the various disclosed sterilant compositions by use of a peristaltic pump.

In some embodiments, the sterilant composition is removed via washing with a buffer composition comprising at least one buffer.

According to the invention, suitable buffers include, without limitation, phosphate buffered saline (PBS), Earle's balanced salt solution (EBSS), Hank's balanced salt solution (HBSS), and Dulbecco's phosphate buffered saline (DPBS).

In some embodiments, the casted construct ECM material is rinsed with a buffer up to six times, including one, two, three, four, five, or six times, with each rinse lasting for about thirty minutes. In an exemplary aspect, it is contemplated that the step of rinsing the casted construct ECM material can comprise rinsing the casted construct ECM material three times, with each rinse lasting for about thirty minutes.

In some embodiments, the buffer composition wash is perfused throughout the casted construct ECM member (or material) vasculature via a peristaltic pump.

In some embodiments, the casted construct ECM vasculature is perfused with a crosslinking composition comprising at least one crosslinking agent.

According to the invention, suitable crosslinking agents include, without limitation, glutaraldehyde, formaldehyde, polyepoxides, diisocyanates, acyl azides, and the aforementioned alcohols and combinations thereof.

In some embodiments, the casted construct ECM material is crosslinked in the range of approximately 0.1-100%.

In some embodiments, the crosslinking agent is continuously perfused in the vasculature for a period of time in the range of approximately 1-48 hours.

In some embodiments, the biomaterial composition disposed within the vasculature of an ECM member comprises at least one ECM-mimicking biomaterial composition.

In some embodiments, the ECM-mimicking biomaterial composition comprises poly(glycerol sebacate) (PGS).

Applicant has found that PGS exhibits numerous beneficial properties that provide several beneficial biochemical actions or activities. The properties and beneficial actions resulting therefrom are discussed in detail below.

PGS Physical Properties

PGS is a condensate of the non-immunogenic compositions glycerol (a simple sugar alcohol) and sebacic acid (a naturally occurring dicarboxylic acid), wherein, glycerol and sebacic acid are readily metabolized when proximate mammalian tissue. The non-immunogenic properties substantially limit the acute inflammatory responses typically associated with other "biocompatible" polymers, such as ePTFE (polytetrafluoroethylene), that are detrimental to bioremodeling and tissue regeneration.

The mechanical properties of PGS are substantially similar to that of biological tissue, indeed, the value of the Young's modulus of PGS is between that of a ligament (in KPa range) and tendon (in GPa range). The strain to failure of PGS is also similar to that of arteries and veins (i.e. over 260% elongation).

The tensile strength of the PGS is at least 0.28±0.004 MPa. The Young's modulus and elongation are at least 0.122±0.0003 and at least 237.8±0.64%, respectively. For applications requiring stronger mechanical properties and a slower biodegradation rate, PGS can be blended with poly (ε-caprolactone) (PCL), i.e. a biodegradable elastomer.

ECM Mimicking Properties/Actions

It has been established that PGS induces tissue remodeling and regeneration when administered proximate to damaged tissue, thus, mimicking the seminal regenerative properties of ECM and, hence, an ECM composition formed therefrom. The mechanism underlying this behavior is deemed to be based on the mechanical and biodegradation kinetics of the PGS. See Sant, et al., *Effect of Biodegradation and de novo Matrix Synthesis on the Mechanical Properties of VIC-seeded PGS-PCL scaffolds*, Acta. Biomater., vol. 9(4), pp. 5963-73 (2013).

In some embodiments, the ECM-mimicking biomaterial composition further comprises at least one of the aforementioned ECM materials.

In some embodiments of the invention, the ECM-mimicking biomaterial composition comprises PGS and poly(ε-caprolactone) (PCL). According to the invention, the addition of PCL to the ECM-mimicking biomaterial composition enhances the structural integrity and modulates the degradation of the composition.

In some embodiments, the ECM/ECM-mimicking biomaterial composition further comprises PCL.

In some embodiments, the ECM-mimicking biomaterial composition comprises poly(glycerol sebacate) acrylate (PGSA), which, according to the invention, can be crosslinked and/or cured via the combination of a photoinitiator and radiation.

According to the invention, suitable photoinitiators for radiation induced crosslinking comprise, without limitation, 2-hydroxy-1-[4-hydroxyethoxy) phenyl]-2-methyl-1-propanone (D 2959, Ciba Geigy), 2,2-dimethoxy-2-phenylacetophenone, titanocenes, fluorinated diaryltitanocenes, iron arene complexes, manganese decacarbonyl, methylcyclopentadienyl manganese tricarbonyl and any organometallatic photoinitiator that produces free radicals or cations.

According to the invention, suitable radiation wavelengths for crosslinking and/or curing the ECM-mimicking biomaterial composition comprise, without limitation, visible light; particularly, radiation in the range of approximately 380-750 nm, and ultraviolet (UV) light, particularly, radiation in the range of 10-400 nm, which includes extreme UV (10-121 nm), vacuum UV (10-200 nm), hydrogen lyman $\alpha$-UV (121-122 nm), Far UV (122-200 nm), Middle UV (200-300 nm), Near UV (300-400 nm), UV-C (100-280 nm), UV-B (280-315 nm) and UV-A (315-400 nm) species of UV light.

In some embodiments, the ECM-mimicking biomaterial composition comprises a co-polymer of PGSA and polyethylene glycol (PEG) diacrylate.

Preferably, the ratio of PGSA to PEG diacrylate used when developing the photocured PGSA hydrogel is proportional to the physical strength of the biomaterial composition, wherein, when the PGSA/PEG diacrylate composition has a ratio of PGSA to PEG diacrylate in the range of 95:05-50:50, the composition exhibits a Young's modulus in the range of approximately 0.5-20 MPa.

According to the invention, the Young's modulus will also vary based on the configuration of the casted constructs, such as the pattern of the vasculature.

In some embodiments of the invention, the ECM-mimicking biomaterial composition comprises an ECM/ECM-mimicking biomaterial composition, e.g. 50% ECM/50% PGS.

In some embodiments, the biomaterial composition disposed within the vasculature of an ECM member comprises a polymeric composition comprising at least one biocompatible polymeric material.

According to the invention, the biocompatible polymeric material can comprise, without limitation, polyglycolide (PGA), polylactide (PLA), poly($\epsilon$-caprolactone) (PCL), poly dioxanone (a polyether-ester), poly lactide-co-glycolide, polyamide esters, polyalkalene esters, polyvinyl esters, polyvinyl alcohol, and polyanhydrides, and like polymers.

The biocompatible polymeric material can also comprise, without limitation, natural polymeric materials, including, without limitation, polysaccharides (e.g. starch and cellulose), proteins (e.g., gelatin, casein, silk, wool, etc.), and polyesters (e.g., polyhydroxyalkanoates).

In some embodiments of the invention, the biocompatible polymeric material comprises, without limitation, polyhydroxyalkonates (PHAs), polylactides (PLLA) and polyglycolides (PLGA) and their copolymers, for example poly($\epsilon$-caprolactone-co-glycolide), polyanhydrides, and like polymers.

According to the invention, biocompatible polymeric materials can also comprise a hydrogel composition, including, without limitation, polyurethane, poly(ethylene glycol), poly(propylene glycol), poly(vinylpyrrolidone), xanthan, methyl cellulose, carboxymethyl cellulose, alginate, hyaluronan, poly(acrylic acid), polyvinyl alcohol, acrylic acid, hydroxypropyl methyl cellulose, methacrylic acid, $\alpha\beta$-glycerophosphate, $\kappa$-carrageenan, 2-acrylamido-2-methylpropanesulfonic acid, and $\beta$-hairpin peptide.

In some embodiments, the hydrogel composition is crosslinked by an enzymatic composition.

According to the invention, suitable crosslinking enzymatic compositions comprise, without limitation, transglutaminase, lysyl oxidase and riboflavin.

In some embodiments, the hydrogel composition is crosslinked and/or cured via exposure to radiation.

In some embodiments, the radiation comprises one of the aforementioned radiation wavelengths.

In some embodiments, the hydrogel composition comprises at least one aforementioned photoinitiator.

In some embodiments, the polymeric composition is plasma treated to accommodate hygroscopic agents.

In some embodiments, the polymeric composition comprises a thermosensitive chitosan hydrogel composition.

In some embodiments, the thermosensitive chitosan composition comprises a chitosan/glycerophosphate composition.

In some embodiments, the thermosensitive chitosan composition sets and/or gelates at a temperature in the range of 30-40° C.

Chitosan (including a thermosensitive chitosan composition) exhibits a wide range of favorable biochemical properties that make it an outstanding agent for use in the medical field. The biochemical properties of chitosan, which are discussed below, include biocompatibility, biodegradability and non-toxicity. Additional properties, such as analgesic, hemostatic, antimicrobial, and antioxidant have also been reported. See Aranaz, et al., *Functional Characterization of Chitin and Chitosan, Current Chemical Biology*, vol. 3, pp. 203-230 (2009); and Kumar M N V R, *A Review of Chitin and Chitosan Applications*, React. Funct. Polm., vol. 46, pp. 1-27 (2000).

Biodegradability of Chitosan

Although chitosan is absent from mammals, chitosan can be readily degraded in vivo by several proteases (lysozyme, papain, pepsin, etc.). The biodegradation of chitosan leads to the release of non-toxic oligosaccharides of variable length, which can be subsequently incorporated to glycosaminoglycans and glycoproteins, to metabolic pathways or be excreted. See Pangburn, et al., *Lysozyme Degradation of Partially Deacetylated Chitin, its Films and Hydrogels*, Biomaterials, vol. 3(2), pp. 105-108 (1982).

Biocompatibility of Chitosan

Chitosan also exhibits very good compatibility; particularly, cytocompatibility. The enhanced cytocompatibility of chitosan has been proven in vitro with myocardial, endothelial and epithelial cells, fibroblast, hepatocytes, chondrocytes and keratinocytes. See Chatelet, et al., *Influence of the Degree of Acetylation on Some Biological Properties of Chitosan Films*, Biomaterials, vol. 22(3), pp. 261-268 (2001).

Analgesic Properties of Chitosan

Chitosan exhibits very favorable analgesic properties (or effects). Okamoto, et al. specifically studied the analgesic effect of chitosan on inflammatory pain due to intraperitoneal administration of acetic acid. See Okamoto, et al., *Analgesic Effects of Chitin and Chitosan*, Carbohyd. Poly., vol. 49, pp. 249-252 (2002).

Okamoto, et al. found that, due to its polycationic nature, the free primary amino groups of chitosan can protonate in the presence of proton ions and, thereby, reduce the pH, which is a primary cause of the analgesic properties. From experimental data, it was also concluded that the analgesic effect was due primarily to the absorption of bradykinin, one of the main components (or substances) related to pain.

Hemostatic Properties of Chitosan

Chitosan, as well as sulphated chitosan oligomers, further exhibits anticoagulant activity. The anticoagulant activity of chitosan is deemed to be related to its positive charge, since red blood cells' membranes are negatively charged. See Rao, et al., *Use of Chitosan as Biomaterial: Studies on its Safety and Hemostatic Potential*, J. Biomed. Mat. Res., vol. 34, pp. 21-28 (1997).

Permeation Enhancing Properties of Chitosan

Chitosan also acts as a permeation enhancer by opening epithelial tight junctions. The mechanism underlying this behavior is deemed to be based on the interaction of positively charged chitosan and the cell membrane resulting in a reorganization of the tight junction-associated proteins. See Smith, et al., *Effect of Chitosan on Epithelial Cell Tight Junctions*, Pharm. Res., vol. 21(1), pp. 43-49 (2004).

Antimicrobial Properties of Chitosan

Chitosan also exhibits antimicrobial activity against different groups of microorganisms, such as bacteria, yeast, and fungi. Two main mechanisms have been suggested as the cause of the inhibition of microbial cells by chitosan.

The first mechanism comprises the interaction with anionic groups on the cell surface due to chitosan's polycationic nature, which causes the formation of an impermeable layer around the cell.

The second mechanism involves the inhibition of the RNA and protein synthesis by permeation into the cell nucleus. See Liu et al., *Antibacterial Action of Chitosan and Carboxymethylated Chitosan*, J. Appl. Polym. Sci., vol. 79(7), pp. 1324-1335 (2001).

Antioxidative Properties of Chitosan

Chitosan has also shown a significant scavenging capacity against different radical species; the results being comparable to those obtained with commercial antioxidants. See Park, et al., *Free Radical Scavenging Activities of Differently Deacetylated Chitosans*, Carbohyd. Polym., vol. 55(1), pp. 17-22 (2004).

Tissue Repair of Chitosan

By virtue of the above discussed properties of chitosan, chitosan can and, in most instances, will enhance the repair of damaged tissue. Indeed, it has been found that chitosan activates immunocytes and inflammatory cells, such as PMN, macrophage, fibroblasts and endothelial cells. See Ueno, et al., *Topical Formulations and Wound Healing Applications of Chitosan*, Adv. Drug Del. Res., vol. 52, pp. 105-115 (2001).

Chitosan oligomers have also exhibited tissue repair properties. It has been suggested that the tissue repair properties are due to their ability to stimulate fibroblast production by affecting the basic fibroblast growth factor. Subsequent collagen production further facilitates the formation of connective tissue.

In some embodiments, the biomaterial composition disposed within the vasculature of the ECM member comprises an ECM composition comprising at least one of the aforementioned ECM materials.

In some embodiments, the ECM material is crosslinked via a crosslinking agent.

According to the invention, suitable crosslinking agents include, without limitation, glutaraldehyde, formaldehyde, polyepoxides, diisocyanates, acyl azides, and the aforementioned alcohols.

In some embodiments, the ECM material is enzymatically crosslinked.

According to the invention, suitable agents for enzymatic crosslinking comprise, without limitation, transglutaminase, lysyl oxidase and riboflavin.

In some embodiments, the ECM material is crosslinked and/or cured via exposure to radiation.

In some embodiments, the radiation comprises one of the aforementioned wavelengths.

In some embodiments, the casted construct comprises at least one coating.

Suitable coatings are disclosed in Co-Pending application Ser. Nos. 14/566,155, 14/566,306 and 14/566,209, which are incorporated by reference herein in their entirety.

In some embodiments, the coating comprises an ECM composition comprising at least one of the aforementioned ECM materials.

In some embodiments, the coating comprises a biodegradable polymeric composition comprising one of the aforementioned polymeric compositions.

In some embodiments, the coating comprises one of the aforementioned ECM-mimicking biomaterial compositions.

In some embodiments, the coating comprises one of the aforementioned ECM/ECM-mimicking biomaterial compositions.

In some embodiments, the coating comprises a blend of the aforementioned ECM and/or polymeric compositions and/or ECM-mimicking biomaterial compositions and/or ECM/ECM-mimicking biomaterial compositions.

In some embodiments of the invention, the casted constructs further comprise an outer reinforcing structure, such as disclosed in Co-pending U.S. application Ser. No. 14/337,863, filed on Jul. 22, 2014, and Ser. Nos. 14/554,730, 14/554,795 and 14/554,847, filed on Nov. 26, 2014, which are incorporated by reference herein in their entirety.

According to the invention, the reinforcing structure can comprise a wound member or strand configuration, i.e. a thin strand wound around the outer surface of the tubular member, such as disclosed in Co-Pending application Ser. No. 14/337,863 or a mesh structure, such as disclosed in Co-Pending application Ser. Nos. 14/554,730, 14/554,795 and 14/554,847.

In some embodiments of the invention, the reinforcing structure comprises a mesh or woven structure.

In some embodiments of the invention, the reinforcing structure comprises one of the aforementioned ECM materials.

In some embodiments, the reinforcing structure comprises one of the aforementioned polymeric compositions.

In some embodiments of the invention, the reinforcing structure comprises one of the aforementioned ECM-mimicking biomaterial compositions.

In some embodiments of the invention, the reinforcing structure comprises one of the aforementioned ECM/ECM-mimicking biomaterial compositions.

In some embodiments of the invention, the reinforcing structure comprises a biocompatible metal, such as stainless steel and Nitinol®.

As indicated above, in some embodiments of the invention, the ECM member(s) and/or biomaterial composition(s) and/or coating(s) and/or reinforcing structure(s) and, hence, casted construct formed therefrom or therewith includes at least one additional biologically active agent or composition, i.e. an agent that induces or modulates a physiological or biological process, or cellular activity, e.g., induces proliferation, and/or growth and/or regeneration of tissue.

Suitable biologically active agents include any of the aforementioned biologically active agents, including, without limitation, the aforementioned cells, proteins and growth factors.

In some embodiments, the ECM member(s) and/or biomaterial composition(s) and/or coating(s) and/or reinforcing structure(s) and, hence, casted construct formed therefrom or therewith includes at least one pharmacological agent or composition (or drug), i.e. an agent or composition that is capable of producing a desired biological effect in vivo, e.g., stimulation or suppression of apoptosis, stimulation or suppression of an immune response, etc.

Suitable pharmacological agents and compositions include any of the aforementioned agents, including, without limitation, antibiotics, anti-viral agents, analgesics, steroidal anti-inflammatories, non-steroidal anti-inflammatories, anti-neoplastics, anti-spasmodics, modulators of cell-extracellular matrix interactions, proteins, hormones, enzymes and enzyme inhibitors, anticoagulants and/or anti-thrombic agents, DNA, RNA, modified DNA and RNA, NSAIDs, inhibitors of DNA, RNA or protein synthesis, polypeptides, oligonucleotides, polynucleotides, nucleoproteins, compounds modulating cell migration, compounds modulating proliferation and growth of cells and/or tissue, and vasodilating agents.

In some embodiments of the invention, the pharmacological agent comprises a statin, i.e. a HMG-CoA reductase inhibitor. According to the invention, suitable statins include, without limitation, atorvastatin (Lipitor®), cerivastatin, fluvastatin (Lescol®), lovastatin (Mevacor®, Altocor®, Altoprev®), mevastatin, pitavastatin (Livalo®, Pitava®), pravastatin (Pravachol®, Selektine®, Lipostat®), rosuvastatin (Crestor®), and simvastatin (Zocor®, Lipex®). Several actives comprising a combination of a statin and another agent, such as ezetimbe/simvastatin (Vytorin®), are also suitable.

Applicant has found that the noted statins exhibit numerous beneficial properties that provide several beneficial biochemical actions or activities. Among the beneficial biochemical actions, Applicant has found that when a statin is added to ECM (wherein a statin augmented ECM member or casted construct is formed) and the statin augmented ECM member is administered to damaged tissue, the statin interacts with the cells recruited by the ECM, wherein the statin augmented ECM member modulates inflammation of the damaged tissue by modulating several significant inflammatory processes, including restricting expression of monocyte chemoattractant protein-1 (MCP-1) and chemokine (C—C) motif ligand 2 (CCR2).

Further beneficial actions are discussed in detail in Applicant's Co-Pending application Ser. No. 13/328,287, filed on Dec. 16, 2011, Ser. No. 13/373,569, filed on Sep. 24, 2012 and Ser. No. 13/782,024, filed on Mar. 1, 2013; which are incorporated by reference herein in their entirety.

Additional suitable pharmacological agents and compositions that can be delivered within the scope of the invention are disclosed in Pat. Pub. Nos. 20070014874, 20070014873, 20070014872, 20070014871, 20070014870, 20070014869, and 20070014868; which are expressly incorporated by reference herein in its entirety.

In some embodiments of the invention, the biologically active agent comprises a protein selected from the group comprising, without limitation, collagen (types I-V), proteoglycans, glycosaminoglycans (GAGs), glycoproteins, cytokines, cell-surface associated proteins, and cell adhesion molecules (CAMs).

In some embodiments, the biologically active agent provides a structural support scaffold. Suitable bioactive agents include, without limitation, elastin and ECM having additional GAG content, such as additional hyaluronic acid and/or chondroitin sulfate.

According to the invention, the biologically active and pharmacological agents referenced above can comprise various forms. In some embodiments of the invention, the biologically active and pharmacological agents, e.g. simvastatin, comprise microcapsules that provide delayed delivery of the agent contained therein.

In some embodiments, the ECM member(s) and/or biomaterial composition(s) and/or coating(s) and/or reinforcing structure(s) and, hence, casted construct formed therefrom or therewith provides a single-stage agent delivery profile, i.e. comprise a single-stage delivery vehicle, wherein a modulated dosage of an aforementioned biologically active and/or pharmacological agent is provided.

According to the invention, the term "modulated dosage" as used herein, and variants of this language generally refer to the modulation (e.g., alteration, delay, retardation, reduction, etc.) of a process involving different eluting or dispersal rates of an agent within biological tissue.

In some embodiments, the single-stage delivery vehicle comprises encapsulated particulates of a biologically active and/or pharmacological agent.

In some embodiments, the encapsulation composition comprises one of the aforementioned ECM compositions.

In some embodiments, the encapsulation composition comprises one of the aforementioned polymeric compositions.

In some embodiments, the encapsulation composition comprises one of the aforementioned ECM-mimicking biomaterial compositions.

In some embodiments, the encapsulation composition comprises one of the aforementioned ECM/ECM-mimicking biomaterial compositions.

In some embodiments, the encapsulation composition comprises an osmotic fluctuation inducing composition. According to the invention, suitable osmotic fluctuation inducing compositions include, without limitation, PEG, alginate and dextran.

According to the invention, the term "osmotic fluctuation" as used herein, and variants of this language generally refer to the modulation of the osmotic pressure gradient across a defined barrier.

For example, as is well known in the art, alginate is capable of absorbing 200-300 times its weight in water, which substantially increases the osmotic pressure gradient of the alginate. The increased osmotic pressure gradient of the alginate results in a rapid dispersal of an agent therefrom.

In some embodiments of the invention, the ECM member(s) and/or biomaterial composition(s) and/or coating(s) and/or reinforcing structure(s) and, hence, casted construct formed therefrom or therewith provides a multi-stage agent delivery profile, i.e. comprise a multi-stage agent delivery vehicle, wherein a plurality of the aforementioned biologically active and/or pharmacological agents are administered via a modulated dosage. By way of example, in some embodiments, the multi-stage delivery vehicle comprises encapsulated particulates comprising an antibiotic composition encapsulated in an alginate composition having a statin incorporated therein, which provides a tiered modulated agent delivery.

In some embodiments, the multi-stage agent delivery vehicle comprises a combination of different biologically active and/or pharmacological agents. By way of example, in some embodiments, the multi-stage delivery vehicle comprises encapsulated particulates comprising an encapsulated growth factor concomitantly administered with an encapsulated anti-inflammatory.

In some embodiments, the multi-stage delivery vehicle comprises a plurality of different biologically active and/or pharmacological agents encapsulated in different encapsulation compositions. By way of example, in some embodiments, the multi-stage delivery vehicle comprises encapsulated particulates comprising a growth factor encapsulated in alginate composition and a pharmacological agent encapsulated in a polyglycolide composition.

According to the invention and indicated above, upon disposing a casted construct of the invention proximate damaged or diseased biological tissue, "modulated healing" is effectuated.

The term "modulated healing", as used herein, and variants of this language generally refer to the modulation (e.g., alteration, delay, retardation, reduction, etc.) of a process involving different cascades or sequences of naturally occurring tissue repair in response to localized tissue damage or injury, substantially reducing their inflammatory effect. Modulated healing, as used herein, includes many different biologic processes, including epithelial growth, fibrin deposition, platelet activation and attachment, inhibition, proliferation and/or differentiation, connective fibrous tissue production and function, angiogenesis, and several stages of acute and/or chronic inflammation, and their interplay with each other.

For example, in some embodiments, the ECM member and/or biomaterial composition and/or coating and/or reinforcing structure and, hence, casted construct formed therefrom or therewith is specifically formulated (or designed) to alter, delay, retard, reduce, and/or detain one or more of the phases associated with healing of damaged tissue, including, but not limited to, the inflammatory phase (e.g., platelet or fibrin deposition), and the proliferative phase when in contact with biological tissue.

In some embodiments of the invention, "modulated healing" means and includes the ability of ECM member(s) and/or biomaterial composition(s) and/or coating(s) and/or reinforcing structure(s) and, hence, casted constructs formed therewith to restrict the expression of inflammatory components. By way of example, according to the invention, when an ECM member and/or biomaterial composition and/or coating and/or reinforcing structure and, hence, casted construct formed therewith comprises a statin augmented ECM composition, i.e. a composition comprising an ECM and an exogenously added statin, and the casted construct is disposed proximate damaged biological tissue, the casted construct restricts expression of monocyte chemoattractant protein-1 (MCP-1) and chemokine (C—C) motif ligand 2 (CCR2).

In some embodiments, "modulated healing" means and includes the ability of an ECM member and/or biomaterial composition and/or coating and/or reinforcing structure and, hence, casted construct formed therefrom or therewith to alter a substantial inflammatory phase (e.g., platelet or fibrin deposition) at the beginning of the tissue healing process. As used herein, the phrase "alter a substantial inflammatory phase" refers to the ability of a casted construct to substantially reduce the inflammatory response at an injury site when in contact with biological tissue.

In such an instance, a minor amount of inflammation may ensue in response to tissue injury, but this level of inflammation response, e.g., platelet and/or fibrin deposition, is substantially reduced when compared to inflammation that takes place in the absence of a casted construct of the invention.

The term "modulated healing" also refers to the ability of an ECM member and/or biomaterial composition and/or coating and/or reinforcing structure and, hence, casted construct formed therewith to induce host cell and/or tissue proliferation, bioremodeling, including neovascularization, e.g., vasculogenesis, angiogenesis, and intussusception, and regeneration of tissue structures with site-specific structural and functional properties.

Thus, in some embodiments, the term "modulated healing" means and includes the ability of ECM member(s) and/or biomaterial composition(s) and/or coating(s) and/or reinforcing structure(s) and, hence, casted constructs formed therewith to modulate inflammation and/or induce host cell and/or tissue proliferation and remodeling. Again, by way of example, according to the invention, when an ECM member and/or biomaterial composition and/or coating and/or reinforcing structure and, hence, casted construct formed therewith comprises a statin augmented ECM composition, i.e. a composition comprising an ECM and an exogenously added statin, and the casted construct is disposed proximate damaged biological tissue, the stain interacts with cells recruited by the ECM, wherein the casted construct modulates inflammation by, among other actions, restricting expression of monocyte chemoattractant protein-1 (MCP-1) and chemokine (C—C) motif ligand 2 (CCR2) and induces cell and/or tissue proliferation, bioremodeling and regeneration of tissue structures with site-specific structural and functional properties.

By way of a further example, according to the invention, when a casted construct comprises a growth factor augmented ECM composition, i.e. a composition comprising an ECM and an exogenously added growth factor, e.g. TGF-$\beta$, is disposed proximate damaged biological tissue, the growth factor similarly interacts with the ECM and cells recruited by the ECM, wherein the casted construct modulates inflammation and induces cell and/or tissue proliferation, bioremodeling and regeneration of tissue.

In some embodiments, when a casted construct is disposed proximate biological tissue modulated healing is effectuated through the structural features of the casted construct. The structural features provide the spatial temporal and mechanical cues to modulate cell polarity and alignment. The structural features further modulate cell proliferation, migration and differentiation thus modulating the healing process.

In some embodiments, the casted constructs provide spatial temporal and mechanical cues.

In some embodiments, the casted constructs are incubated in a macerating composition to degrade the ECM member.

According to the invention, suitable macerating compositions include, without limitation, sodium hydroxide (NaOH), Hydrochloric Acid (HCl), Sulfuric Acid ($S_2HO_4$), Potassium Hydroxide (KOH), chemical acid solutions having a pH at least lower than 4 and chemical base solutions having a pH at least higher than 10.

In some embodiments, the casted constructs are macerated enzymatically.

In some embodiments, the casted constructs are between 0.1-100% macerated.

In some embodiments, the casted constructs are completely macerated to provide a biomaterial composition alone, wherein the biomaterial composition is substantially devoid of the surrounding ECM member.

In some embodiments of the invention, the tensile strength of the casted construct is preferably in the range of approximately 200-5000 KPa.

In some embodiments of the invention, the Young's modulus of the casted construct is preferably in the range of approximately 30-1000 KPa.

In some embodiments of the invention, the casted construct comprises a porosity in the range of 10-90%.

According to the invention, the biomaterial compositions of the invention can be delivered into the ECM member vasculature by various conventional means.

In some embodiments, the biomaterial composition is injected into at least one artery.

In some embodiments, the biomaterial composition is injected into at least one venous vessel.

In some embodiments, the venous vessel comprises a blood vessel.

In some embodiments, the venous vessel comprises a lymphatic vessel.

In some embodiments, the injection into a venous vessel is performed via a retrograde injection, wherein the composition flow direction is oriented to bypass the native valves present in the venous vessels that obstruct anterograde injection.

In some embodiments, the total volume of the biomaterial composition is administered in a single continuous injection.

In some embodiments, the total volume of the biomaterial composition is administered via a plurality of injections.

In some embodiments, the vasculature of the ECM member is perfused via a peristaltic apparatus.

Referring now to FIG. 1, there is shown an illustration of a segment of the vasculature 10 of a small intestine. As illustrated in FIG. 1, the vasculature 10 comprises a primary mesentery artery 12 and a plurality of capillaries 14.

Figure 2:
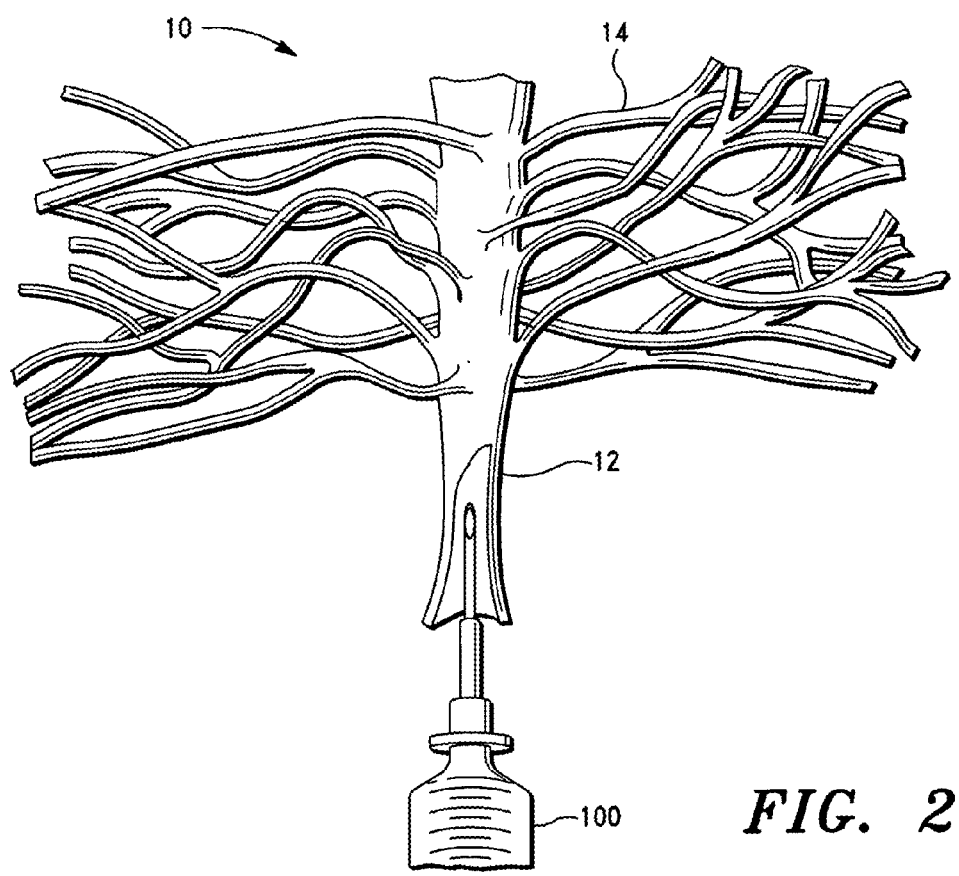
FIG. 2 is an illustration of a mammalian small intestine vasculature shown in FIG. 2, being infused with a biocompatible composition, in accordance with the invention.

Referring now to FIG. 2, there is shown the small intestine vasculature 10 receiving an anterograde injection of an aforementioned biomaterial composition from injection means 100.

Figure 3:
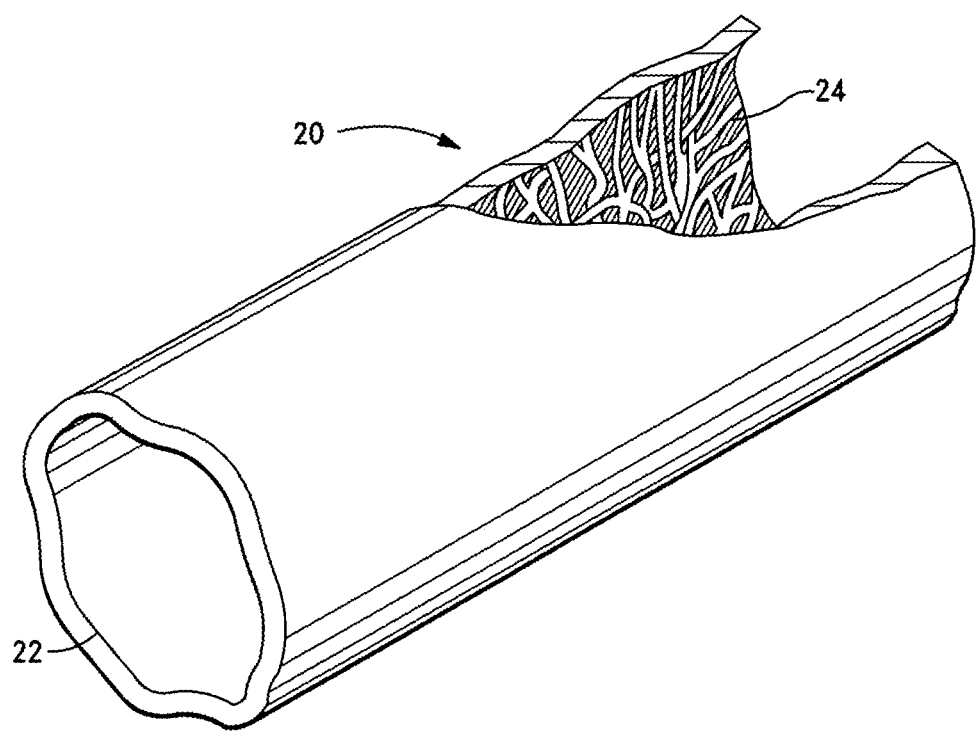
FIG. 3 is a perspective partial sectional view of a casted construct, showing the vasculature thereof, in accordance with the invention.

Referring now to FIG. 3, there is shown one embodiment of a seamless tubular casted construct 20 of the invention, which, as indicated above, in some embodiments comprises a section of small intestine. As illustrated in FIG. 3, the tubular construct 20 includes a lumen 22 and a plurality of capillaries 24.

According to the invention, in some embodiments, casted construct 20 can similarly comprise various dimensions to accommodate various biological structures and applications.

EXAMPLES

The following examples are provided to enable those skilled in the art to more clearly understand and practice the present invention. They should not be considered as limiting the scope of the invention, but merely as being illustrated as representative thereof.

Example 1

Figure 4:
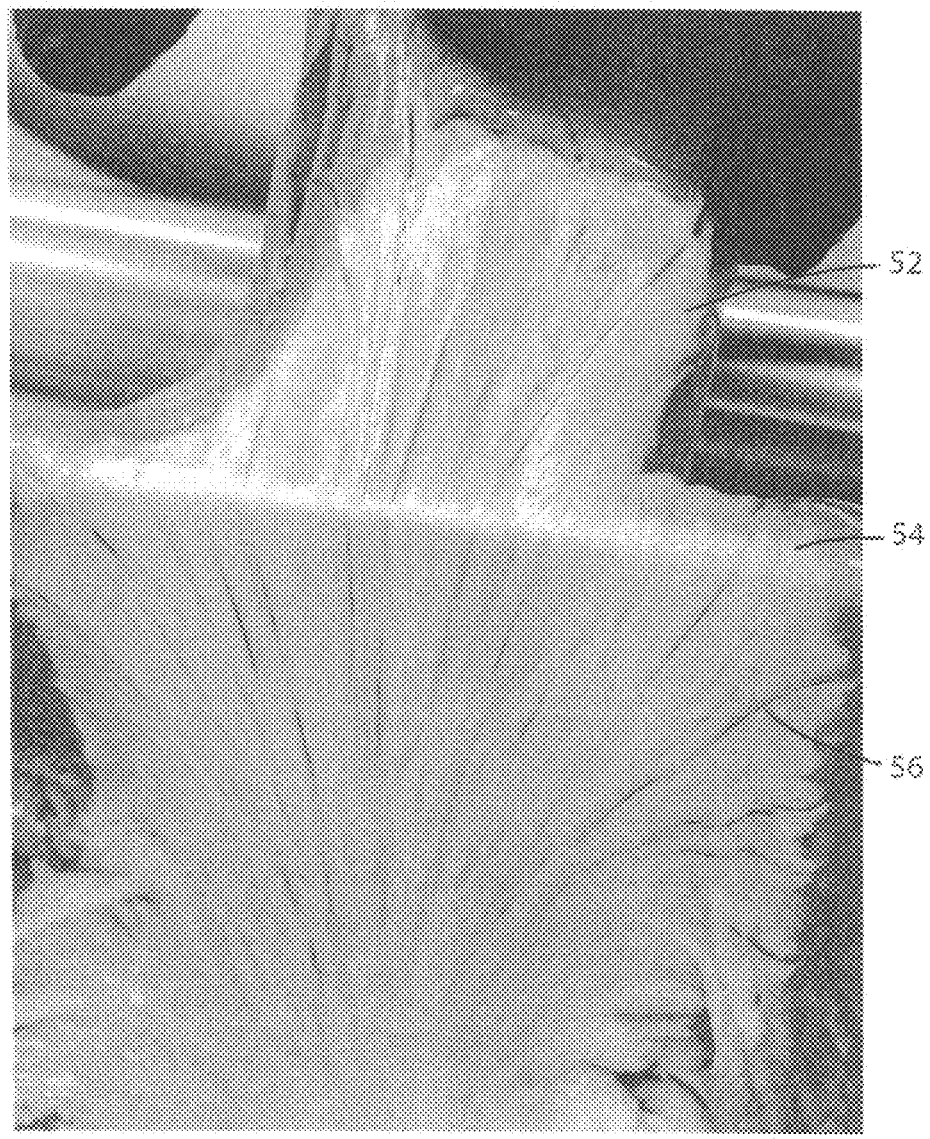
FIG. 4 is a photograph depicting a segment of resected porcine small intestine, showing the vasculature thereof, in accordance with the invention.
Figure 6:
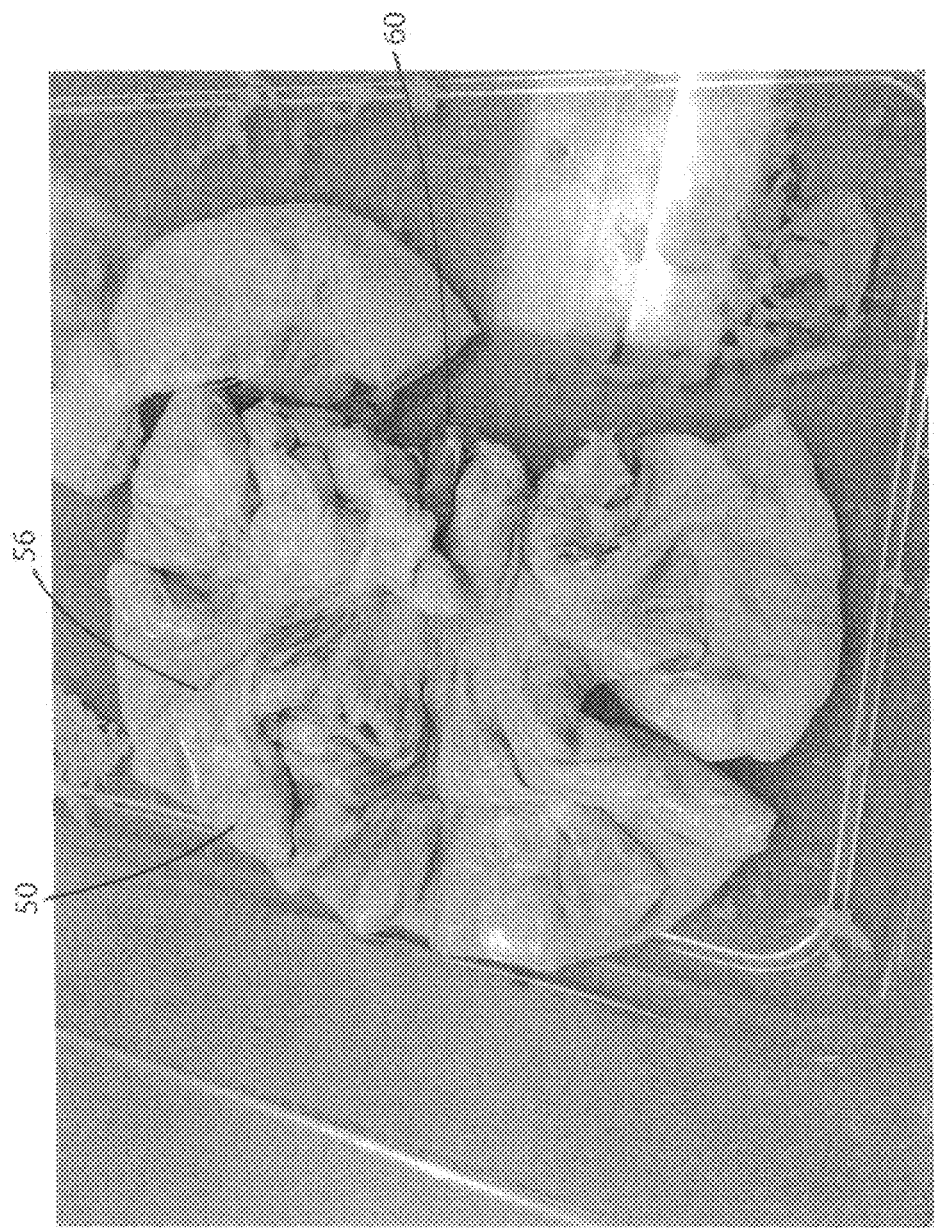
FIG. 6 is a photograph depicting the full decellularized, sterile resected porcine small intestine, showing the vasculature thereof infused with a tracing composition via anterograde injection into the main artery, in accordance with the invention.

Referring now to FIG. 4, there is shown a portion 52 of the resected section of porcine small intestine 50 shown in FIG. 6. As illustrated in FIG. 4, the small intestine portion 52 includes the mesentery 54 and capillaries 56.

After resection, the section of the small intestine 50 was processed, i.e. rinsed, with a gentle detergent (0.5% Triton X-100/0.5% Sodium Deoxycholate in 5 mM EDTA in DPBS) for 24 hours and thereafter rinsed three times in DPBS (as discussed above), via anterograde injection of the respective solutions into the primary mesentery artery 60 (see FIG. 6). The rinses were followed by an additional anterograde injection of a sterilant composition (2.0% peracetic acid in 5% ethyl alcohol) into the mesentery artery 60.

The addition of the sterilant was followed by an additional rinse step (three washes in DPBS).

Figure 5:
FIG. 5 is a photograph depicting a decellularized, sterile segment of the resected porcine small intestine, showing the vasculature thereof infused with a tracing composition, in accordance with the invention.

Referring now to FIG. 5, the additional rinse step was followed by an anterograde injection of a tracing composition (0.4% Trypan Blue) into primary mesentery artery 60. As illustrated in FIGS. 5 and 6, the tracing composition was visibly present in the submucosa capillaries 55 and the mesentery capillaries 56.

The resultant structure thus comprised a sterilized and acellular section of porcine small intestine 50 (see FIG. 6).

The example thus confirms that biological tissue can be sterilized and decellularized via the anterograde injection of detergent and sterilant compositions into the vasculature.

The example further confirms that a biomaterial composition can and will perfuse into the vasculature of biological tissue.

Example 2

Figure 7:
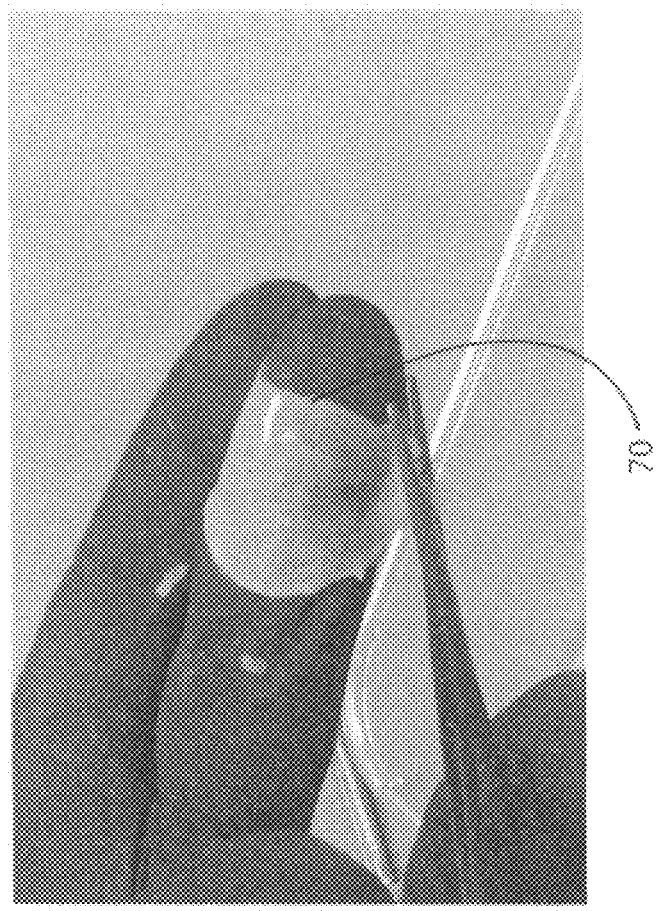
FIG. 7 is a photograph depicting a decellularized, sterile tubular segment of porcine small intestine, in accordance with the invention.

Referring now to FIG. 7, a segment 70 of the sterilized and acellular section of porcine small intestine described in Example 1 was used to form a tubular seamless casted construct. As indicated above, the porcine small intestine segment 70 can be trimmed to any length to accommodate various applications.

Example 3

Figure 8:
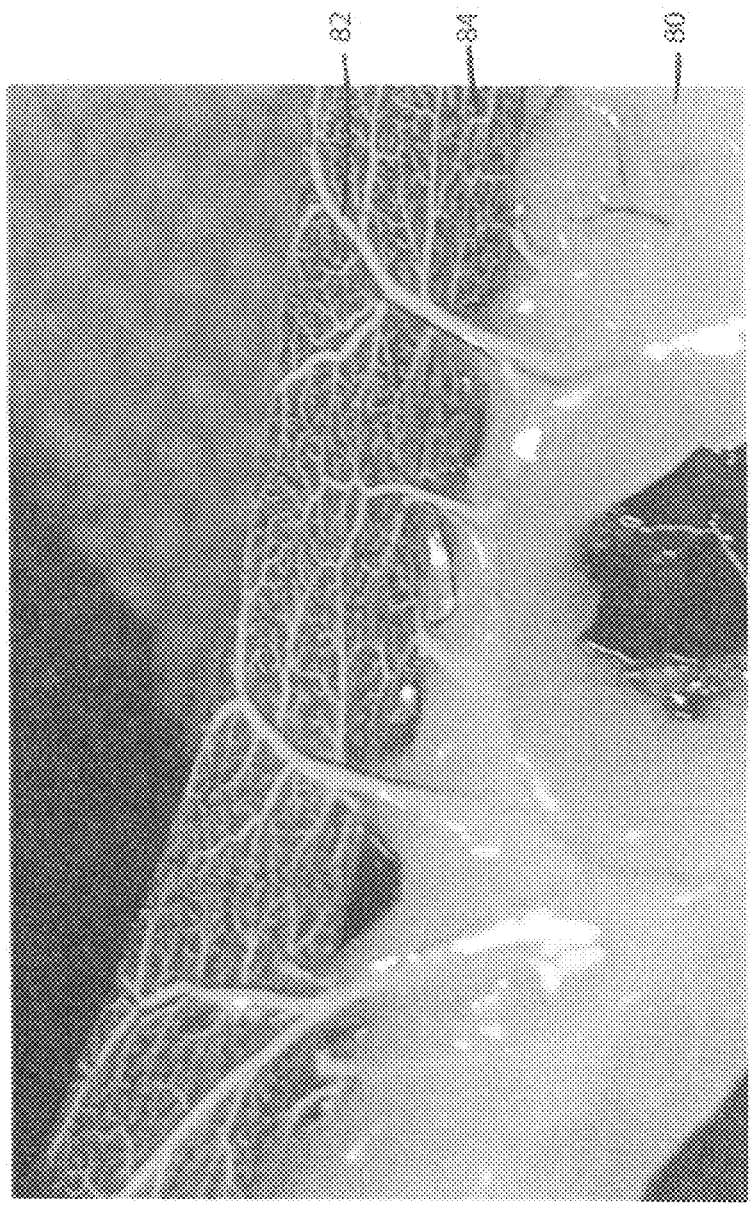
FIG. 8 is a photograph depicting a decellularized, sterile resected rabbit small intestine with the vasculature infused with a biomaterial composition, in accordance with the invention.

A segment of rabbit small intestine was resected and processed in a manner similar to the porcine small intestine in Example 1. Referring now to FIG. 8, the vasculature 82 of the sterilized and acellular section of rabbit small intestine 80 was then infused with a polymeric composition of the invention (shown in yellow); in this instance, a polymeric composition comprising polyurethane.

The resultant structure 84 comprised a sterilized and acellular ECM member with a biomaterial composition perfused within the vasculature 82.

According to the invention, the casted constructs 70, 84 described above and shown in FIGS. 7 and 8, when disposed proximate damaged tissue, modulate inflammation of the damaged tissue by, among other actions, restricting expression of MCP-1 and CCR2, and induce cell and/or tissue proliferation, bioremodeling and regeneration of tissue structures with site-specific structural and functional properties.

It is to be understood that the casted constructs discussed herein and shown in FIGS. 1-7 are merely examples of the various casted constructs that can be employed within the scope of the invention. The casted constructs shown in FIGS. 1-7 should thus not be construed as limiting the scope of the invention in any manner.

As will be readily appreciated by one having ordinary skill in the art, the casted constructs of the invention can be configured in a variety of shapes and readily employed in various medical procedures, including, without limitation, treatment of coronary and peripheral vascular disease (PVD) in cardiovascular vessels, including, but not limited to, iliacs, superficial femoral artery, renal artery, tibial artery, popliteal artery, etc., deep vein thromboses (DVT), vascular bypasses, and coronary vascular repair.

The casted constructs of the invention can also be configured in a variety of shapes and used to repair, augment, reconstruct or replace other damaged or diseased biological structures and associated tissue, including a pericardium, myocardium, esophagus, trachea, bronchus, ureter, urethra, bile duct, and small and large intestine. The casted constructs can also be readily employed to reconstruct or replace damaged or diseased dura around a spinal cord.

The casted constructs can also be readily employed to form a biomaterial pouch configured to encase an ECM or pharmacological composition, or medical instrument or device, such as a pacemaker, therein. Illustrative pouch configurations are disclosed in U.S. Pat. No. 8,758,448 and Applicant's Co-pending U.S. application Ser. Nos. 13/573,566 and 13/896,424, which are incorporated by reference herein in their entirety.

The casted constructs can also be readily employed to construct a valve conduit that is configured to replace and/or regenerate a damaged and/or defective heart valve. Illustrative valve configurations are disclosed in U.S. Pat. Nos. 8,696,744 and 8,709,076 and Applicant's Co-pending U.S. application Ser. No. 13/804,683, which are incorporated by reference herein in their entirety.

The casted constructs can also be readily employed to construct a valve conduit that is configured to replace a damaged and/or defective vascular structures. Illustrative vascular prostheses are disclosed in U.S. Pat. No. 8,808,363 and Applicant's Co-pending U.S. application Ser. Nos. 14/031,520, 14/337,915 and 14/337,863, which are incorporated by reference herein in their entirety.

One having ordinary skill in the art will thus readily appreciate that the casted constructs of the invention provide numerous advantages over conventional apparatus and structures for repairing and/or regenerating tissue. Among the advantages are the following:

The provision of casted constructs that can be readily and effectively employed to treat various damaged or diseased biological structures and associated tissue;

The provision of casted constructs that can be readily employed to close and maintain closure of openings in biological tissue;

The provision of casted constructs that equal or exceed resilience of prosthetics formed from synthetic compositions, while being configured to induce host cell and/or tissue proliferation, bioremodeling and regeneration of new tissue, and tissue structures with site-specific structural and functional properties;

The provision of casted constructs that provide spatial and mechanical cues that modulate cell polarity, spatial temporal positioning, differentiation, proliferation and migration when in contact with biological tissue; particularly, damaged and/or diseased tissue cells;

The provision of casted constructs that include ECM-mimicking biomaterials that induce host cell and/or tissue proliferation, bioremodeling and regeneration of new tissue, and tissue structures with site-specific structural and functional properties;

The provision of casted constructs that are configured to effectively administer at least one biologically active agent and/or pharmacological agent or composition to a subject's tissue to induce a desired biological and/or therapeutic effect; and Methods of treating damaged biological tissue by administering a tissue prosthesis of the invention thereto.

Without departing from the spirit and scope of this invention, one of ordinary skill can make various changes and modifications to the invention to adapt it to various usages and conditions. As such, these changes and modifications are properly, equitably, and intended to be, within the full range of equivalence of any issued claims.

What is claimed is:

1. A method for treating damaged biological structures and tissue, comprising the steps of:
   providing a tissue prosthesis comprising a reinforced mammalian tissue structure, said mammalian tissue structure comprising sterilized and acellular extracellular matrix (ECM) from a mammalian tissue source, said mammalian tissue structure further comprising an intact, continuous, reinforced, sterilized and acellular internal vasculature, said internal vasculature and mammalian tissue structure being sterilized and decellularized by perfusion of a sterilant into said internal vasculature,
   said vasculature being infused with a polymeric composition comprising a polymeric material selected from the group consisting of polyglycolide (PGA), polylactide (PLA), poly($\epsilon$-caprolactone) (PCL), poly dioxanone, poly lactide-co-glycolide, polyamide esters, polyalkalene esters, polyvinyl esters, polyvinyl alcohol, and polyanhydrides, and mixtures thereof,
   said tissue prosthesis being capable of inducing modulated healing of damaged biological tissue when disposed proximate thereto, said modulated healing comprising modulation of an inflammatory phase of said damaged biological tissue, and induced host cell and tissue proliferation, bioremodeling of said damaged biological tissue, neovascularization and regeneration of new tissue and tissue structures with site-specific structural and functional properties; and
   disposing said tissue prosthesis proximate first damaged tissue of a biological structure, wherein said tissue prosthesis induces said modulated healing of said first damaged tissue.

2. The method of claim 1, wherein said sterilized and acellular ECM comprises a crosslinked sterilized and acellular ECM.

3. The method of claim 1, wherein said mammalian tissue source comprises mammalian tissue selected from the group consisting of small intestine submucosa, urinary bladder submucosa, stomach submucosa, placental tissue, mesothelial tissue, cardiac tissue, kidney tissue, pancreas tissue, and lung tissue.

4. The method of claim 1, wherein said tissue structure comprises a planar tissue structure.

5. The method of claim 1, wherein said tissue structure comprises a seamless tubular tissue structure.

6. The method of claim 5, wherein said seamless tubular tissue structure comprises a segment of a mammalian structure selected from the group consisting of mammalian intestine, umbilical artery, umbilical vein, ureter, mesenteric vessel and jugular vein.

7. The method of claim 5, wherein said seamless tubular tissue structure comprises a segment of adolescent small intestine.

8. The method of claim 1, wherein said polymeric composition further comprises a biologically active agent.

9. The method of claim 8, wherein said biologically active agent comprises a growth factor selected from the group consisting of a transforming growth factor-alpha (TGF-$\alpha$), transforming growth factor-beta (TGF-$\beta$), basic fibroblast growth factor (bFGF), and vascular epithelial growth factor (VEGF).

10. The method of claim 1, wherein said polymeric composition further comprises a pharmacological agent.

11. The method of claim 10, wherein said pharmacological agent comprises a statin selected from the group consisting of atorvastatin, cerivastatin, fluvastatin, lovastatin, mevastatin, pitavastatin, pravastatin, rosuvastatin and simvastatin.

12. The method of claim 10, wherein said pharmacological agent comprises an anti-inflammatory selected from the group consisting of desoximetasone, diftalone, flazalone, ibuprofen, ibuprofen aluminum, ibuprofen piconol, and rimexolone.

13. The method of claim 1, wherein said mammalian tissue structure further comprises a supplemental biologically active agent.

14. The method of claim 13, wherein said supplemental second biologically active agent comprises a basic fibroblast growth factor (bFGF).

* * * * *